(12) United States Patent
Miller

(10) Patent No.: US 11,247,017 B2
(45) Date of Patent: Feb. 15, 2022

(54) CAPSULE HUMIDIFIER

(71) Applicant: Pegasus Research Corporation, Santa Ana, CA (US)

(72) Inventor: Kenneth G. Miller, Santa Ana, CA (US)

(73) Assignee: PEGASUS RESEARCH CORPORATION, Santa Ana, CA (US)

( * ) Notice: Subject to any disclaimer, the term of this patent is extended or adjusted under 35 U.S.C. 154(b) by 627 days.

(21) Appl. No.: 16/196,400

(22) Filed: Nov. 20, 2018

(65) Prior Publication Data

US 2020/0155787 A1    May 21, 2020

(51) Int. Cl.
    *A61M 16/00*    (2006.01)
    *A61M 16/16*    (2006.01)
    *A61M 16/10*    (2006.01)

(52) U.S. Cl.
    CPC ........ *A61M 16/16* (2013.01); *A61M 16/0003* (2014.02); *A61M 16/0057* (2013.01); *A61M 16/109* (2014.02)

(58) Field of Classification Search
    CPC .............. A61M 16/16; A61M 16/0003; A61M 16/109; A61M 16/0057
    See application file for complete search history.

(56) References Cited

U.S. PATENT DOCUMENTS

| | | | | |
|---|---|---|---|---|
| 4,381,267 | A * | 4/1983 | Jackson ................ | A61M 16/16 128/204.13 |
| 4,921,642 | A * | 5/1990 | LaTorraca ......... | A61M 16/1075 128/203.27 |
| 6,367,472 | B1* | 4/2002 | Koch ................ | A61M 16/1075 128/203.12 |
| 2006/0012057 | A1* | 1/2006 | Anthony ............... | A61M 16/16 261/154 |
| 2012/0004499 | A1* | 1/2012 | Ott ........................ | H05B 1/025 600/36 |
| 2019/0240432 | A1* | 8/2019 | Burgess ................. | G01F 1/698 |

* cited by examiner

*Primary Examiner* — Steven O Douglas
(74) *Attorney, Agent, or Firm* — Olson & Cepuritis, Ltd.

(57) ABSTRACT

A breathing gas humidifier capsule having an evaporator module with a heated, hydrophobic liquid water reservoir defined by water vapor-permeable walls. Liquid water in the hydrophobic reservoir is vaporized by a heater and the generated water vapor is entrained in a passing breathing gas stream.

14 Claims, 4 Drawing Sheets

CAPSULE HUMIDIFIER

FIELD OF INVENTION

This invention relates to respiratory therapy devices and, more particularly, to a breathing gas humidifier.

BACKGROUND OF INVENTION

For optimal inhalation therapy, the breathing gas must be warm and humidified. Without humidification the patient's lungs dry out and collapse, sometimes with fatal result, because the upper airways of a patient, i.e., the nose and the mouth, which provide natural humidification, are bypassed when artificial ventilation is utilized.

Currently available respiratory humidifiers can be placed in one of three groups according to method of operation: nebulizing, bubbling and heated evaporation. Nebulizing humidifiers rely on the flow of pressurized breathing gas through an ejector-like element to generate an aerosol spray. With bubbling humidifiers, breathing gas is forced directly through a pool of liquid water. Heated-evaporation humidifiers employ a heated contact chamber, where breathing gas is passed over heated water to absorb water vapor.

A persistent, serious problem with all known humidifiers is condensation or "rainout" in the ventilator circuit downstream of the humidifier. As humidified breathing gas travels through tubing towards the patient, it is cooled by ambient air. Tubing cleanup and system readjustments are all too frequent steps in the maintenance of ventilator circuits. Wet circuits also promote respiratory infections.

While heated evaporation humidifiers are deemed to suffer somewhat less from the rainout problem because rather than entrained droplets, such humidifiers require excessive heating and humidity as the breathing gas travels a relatively long path along the hose leading to the patient. Condensation must be monitored closely to avoid inhalation by the patient. Also, without careful monitoring, the temperature of heated water may rise above acceptable limits and cause dangerous overheating of the breathing gas. Equally dangerous are the steam surges produced when liquid water first contacts a dry heater bed following a disruption in water supply.

Another recognized disadvantage of heated evaporation humidifiers is over-dampening of ventilator pressure waves. For artificial respiration, the large gas volumes required in conventional humidifiers over dampen the pressure waves generated by the ventilator to inflate the patient's lungs.

The present capsule humidifier addresses these and other problems with existing humidifiers and provides an efficient breathing gas humidifier having a relatively small gas volume evaporator module that produces only water vapor and can be situated relatively close to the patient.

SUMMARY OF INVENTION

A breathing gas humidifier capsule comprises an evaporator module which includes an elongated, hollow chamber provided with a breathing gas inlet and a breathing gas outlet. Situated within the hollow chamber is a hydrophobic, water vapor-permeable liquid water reservoir adapted for circulation of liquid water therethrough. A heater is positioned within the liquid water reservoir for vaporizing a portion of the liquid water present.

The humidifier capsule is part of a breathing gas humidifier that includes, in addition to the humidifier capsule and its evaporator module, a temperature sensor in the breathing gas outlet of the capsule, a liquid water flow controller in fluid flow communication with the liquid water inlet of the water vapor-permeable liquid water reservoir in the evaporator module, and a breathing gas temperature controller which is operably connected to the liquid water flow controller, the heater in the evaporator module, and the temperature sensor.

BRIEF DESCRIPTION OF DRAWING

In the drawings,

In FIG. 1 a single block may indicate several individual components and/or circuits which collectively perform a function. A single line may represent several individual signal or energy transmission paths for performing a particular operation.

DESCRIPTION OF PREFERRED EMBODIMENTS

A humidifier embodying the features of the present invention provides efficient, cost-effective temperature and humidity control of breathing gas for inhalation therapy. Humidifiers embodying the present invention greatly reduce the likelihood of operational problems such as rainout and breathing gas overheating.

Figure 1:
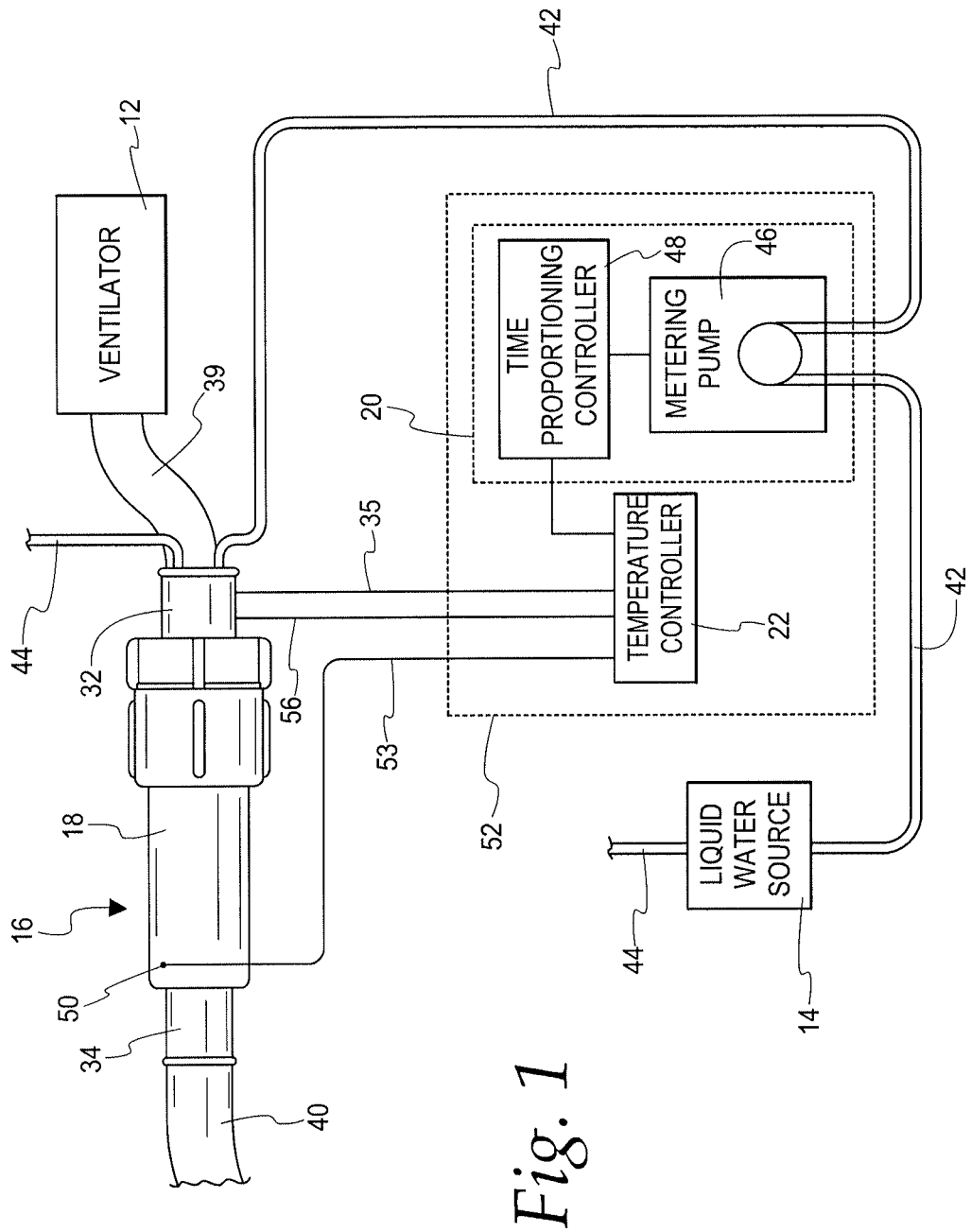
FIG. 1 is a diagram of a breathing gas humidifier utilizing a humidifier capsule embodying the present invention.

Referring to FIG. 1, a humidifier of the present invention is shown connected to a breathing gas source, such as ventilator 12, and a liquid water source 14.

The humidifier includes a humidifier capsule 16 provided with evaporator module 18 which is in confined flow communication with liquid water source 14 and a temperature controller 22 operably connected to breathing gas temperature sensor 50 by cable 53. A pump, such as metering pump 46, circulates liquid water through capsule 16 via liquid water flow passageway 42 and liquid water return passageway 44. Flow controller 20 is operably associated with a metering pump. The liquid water flow to evaporator module 18 can be continuous or intermittent, as desired. Liquid water supplied to evaporator module 18 is vaporized therein, and the produced water vapor is entrapped by a breathing gas passing through capsule 16 as described in greater detail below.

So that breathing gas may pass through evaporator module 18 in capsule 16, breathing gas inlet 32 and breathing gas outlet 34 are provided for capsule 16. Gas inlet 32 is in confined flow communication with ventilator 12 via ventilator gas passageway 39. Breathing gas outlet 34 connects to a patient's "Y" connector (not shown), via an inhalation gas passageway 40.

Flow controller 20 includes a fixed displacement, metering pump such as peristaltic pump 46 which can be operably associated with optional, time-proportioning pump controller 48 if intermittent liquid water flow is desired. Other types of fixed displacement metering pumps suitable for use in the humidifier include diaphragm pumps, piston pumps, bellows-style pumps, and the like.

Metering pump 46 has an adjustable delivery rate which can be continuous or intermittent, as desired. By incorporating an optional timer function, time proportioning controller 48 can serve to turn metering pump 46 on for a fixed time period, and thereby control the total amount of liquid water delivered to evaporator module 18. Controller 48 can accept a time proportion setpoint, which represents the fraction of a given time period (e.g. about 1 hour) that the pump is turned on.

In addition to providing a desired flow rate, metering pump 46 also serves to substantially isolate water source 14 from the breathing gas circuit. With water source 14 isolated, the total volume of space within the breathing circuit, and therefore the related pressure dampening effects, are substantially reduced as compared to conventional humidifiers.

Figure 4:
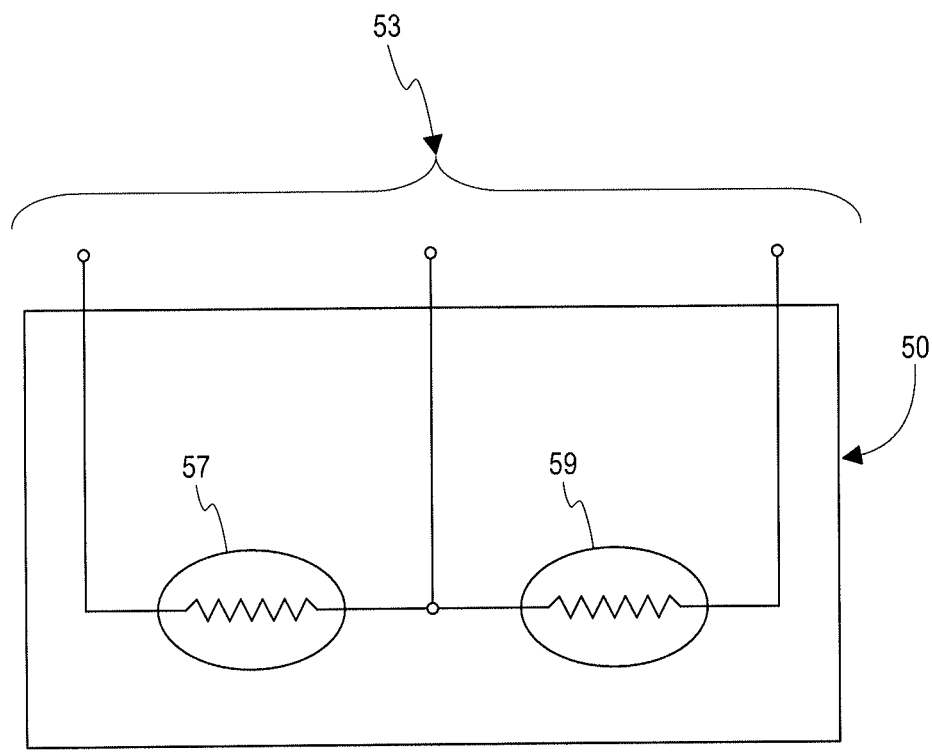
FIG. 4 is a circuit diagram for a preferred breathing gas temperature sensor.

Flow controller 20 is part of the control cascade that includes breathing gas temperature controller 22. Temperature controller 22 can also be characterized as a system control module. Temperature controller 22 is operably connected to flow controller 20, a heater provided within evaporator module 18, and breathing gas temperature sensor 50 positioned at breathing gas outlet. Controller 22 adjusts both the power input to the heater and the setpoint of flow controller 20 in response to changes in breathing gas temperature at sensor 50. Breathing gas temperature sensor 50 preferably comprises dual thermistors as illustrated in FIG. 4. During normal operation, thermistors 57, 59 provide matching outputs to and are monitored by temperature controller 22. An error signal is generated when a matching output is not detected by controller 22. Preferably, thermistors 57, 59 are 100 kΩ Negative Temperature Coefficient (NTC) thermistors operating in a self-heated, steady-state condition.

As indicated by a dashed-line, box 52, the controller elements are preferably combined into a single module. In such arrangement, the circuitry elements of time proportioning controller 48 and temperature controller 22 may share a power source (not shown) as well as other required components.

Optionally temperature controller 22 can be configured to accept via cable 56 a signal from a heater temperature sensor within evaporator module 18. Temperature controller 22 then can use the temperature of the heater as a safety constraint that limits heating power if the heater temperature exceeds a set high limit. Should the flow of liquid water to evaporator module 18 be inadvertently interrupted, such a constraint control feature reduces the risk that evaporator module 18 may generate a surge of steam when the water supply to evaporator module is reestablished.

Figure 2:
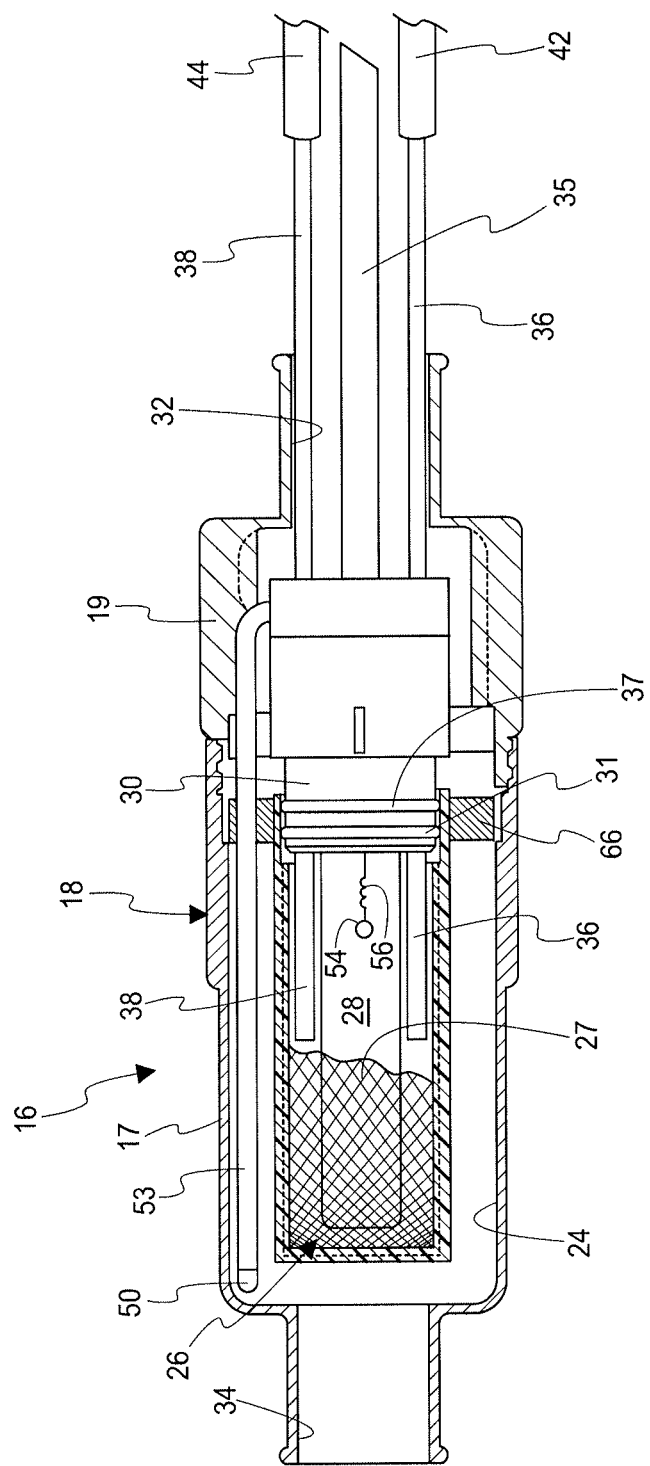
FIG. 2 is a sectional view of a breathing gas humidifier capsule, partly broken away to show interior detail.

FIG. 2 shows the interior detail of evaporator module 18. An elongated, rigid shell 17 open at one end, together with cap 19 therefor, defines a hollow chamber 24 provided with breathing gas inlet 32 and breathing gas outlet 34. A hydrophobic, water vapor permeable reservoir, such as cylindrical liquid water reservoir 26, is defined by a hydrophobic mesh, screen or membrane, and is situated within hollow chamber 24. Both shell 17 and hydrophobic reservoir 26 preferably have a cylindrical configuration and are aligned coaxially to define an annular space therebetween. Cap 19 is threadedly attached to shell 17.

Liquid water inlet 36 to reservoir 26 is operably connected to liquid water flow passageway 42 and supplies liquid water to reservoir 26 from external liquid water source 14. Liquid water outlet 38 is operably connected to liquid water return passageway 44 and provides confined liquid flow communication with liquid water source 14 for the liquid water circulating through reservoir 26 by the action of metering pump 46. The relative positions of liquid water inlet 36 and liquid water outlet 38 are arranged within reservoir 26 so that reservoir 26 is only partially filled with liquid water and maintains a head space for water vapor.

Preferably, the liquid water inlet and the liquid water outlet extend into the liquid water reservoir equally. More preferably, the liquid water reservoir is cylindrical and coaxial with the elongated rigid shell, and the liquid water inlet and the liquid water outlet extend into the longitudinal space defined by the liquid water reservoir a distance which is about one half of the length of the cylindrical liquid water reservoir.

Heater 28 is an electric resistance in the form of an elongated rod, is carried by plug 30, and extends into reservoir 26. Preferably heater 28 is axially aligned with the longitudinal axis of reservoir 26, more preferably coaxial with reservoir 26. In this manner the breathing gas flow is heated outwardly from the center or its flow axis. In this manner, the capsule humidifier temperature remains relatively cool to the touch and safe to the patient. Heater 28 serves to convert a portion of the liquid water present in reservoir 26 to water vapor. The water vapor generated by heater 28 exits reservoir 26 through the hydrophobic mesh or membrane that defines at least a portion of the wall of reservoir 26. The water vapor is entrained by the breathing gas passing through chamber 26 from ventilator 12. A heater temperature sensor, such as thermistor 54, monitors heater temperature and is operably connected to temperature controller 22 by cable 56.

Plug 30 and associated O-rings 31 and 37 around plug 30 provide a liquid-tight seal for reservoir 26.

Power to heater 28 is supplied via power cable 35 from temperature controller 35. Power output of heater 28 usually is in the range of about 30 to about 80 watts, preferably about 50 watts. This relatively low power requirement eliminates temperature spikes in the breathing gas and thus protects the patient.

Temperature sensor 50 for the humidified breathing gas usually is set at a temperature in the range of about 32 degrees C. to about 38 degrees C., preferably about 35 degrees C.

Figure 3:
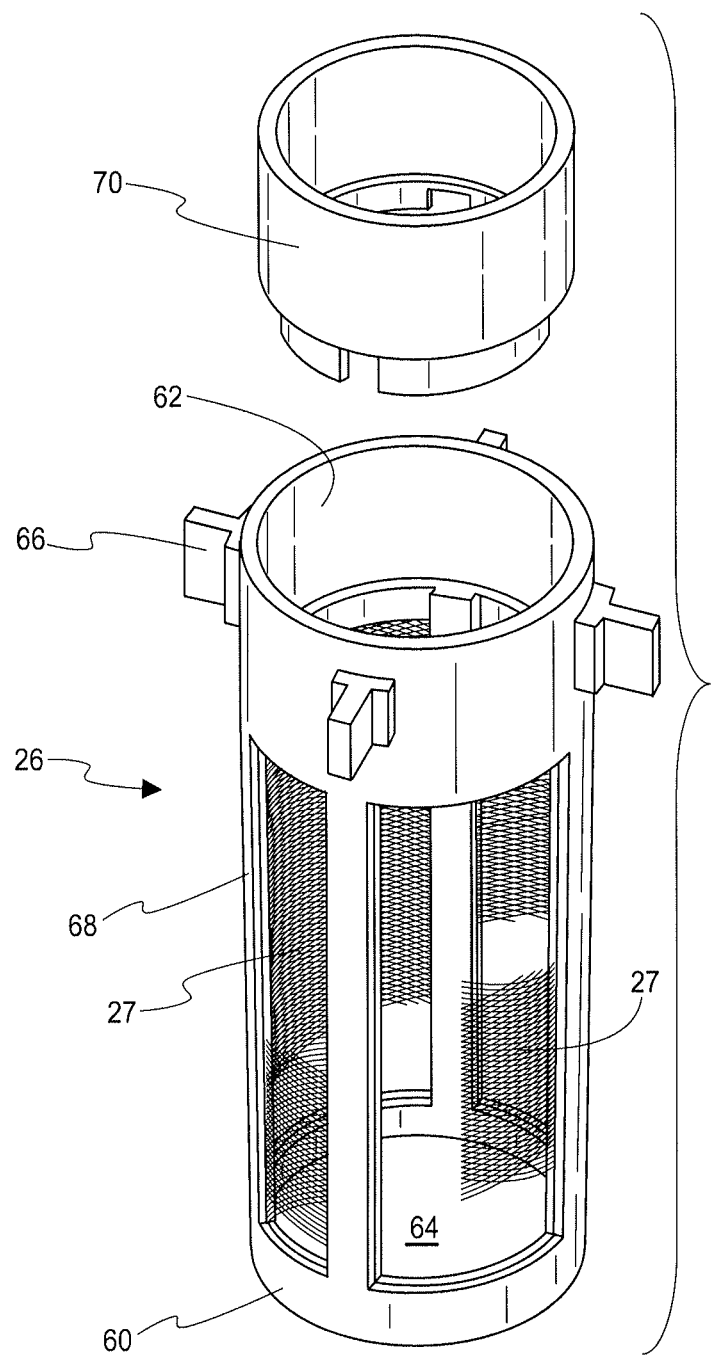
FIG. 3 is an exploded perspective view of a liquid water reservoir within the breathing gas humidifier capsule, partly broken away to show interior detail.

Referring to FIG. 3, liquid water reservoir 26 is a molded cylindrical cage 60 having an open end 62, a closed end 64, and four peripheral spacing lugs such as lug 66. Cylindrical cage 60 defines a plurality of side openings or windows such as window 68. Water vapor permeable membrane or mesh, such as membrane 27, is mounted to the side openings. The water vapor permeable membrane or mesh serves to retain liquid water within reservoir 26 while permitting water vapor to pass through to be entrained in the breathing gas stream from ventilator 12.

Tubular insert 70 is received within open end 62 and serves as a retainer for the water vapor permeable membrane or mesh 27.

The water vapor permeable walls of liquid water reservoir 26, such as mesh 27, are hydrophobic and have a moisture vapor transmission rate (MVTR) of at least 15,500 grams/m$^2$·hr., preferably in the range of about 20,000 to about 60,000 grams/m$^2$·hr. Suitable, water vapor permeable, hydrophobic materials of construction are hydrophobic membranes such as polytetrafluoroethylene filter media, polyarylsulfone filter media, and the like, commercially available from Donaldson Company, Inc., Bloomington, Minn. and Pall Corporation, Port Washington, N.Y.

The water vapor generated within reservoir 26 by heater 28 is entrained by the breathing gas that passes through chamber 24 as indicated hereinabove, and the resulting humidified breathing gas then exits evaporator module via breathing gas outlet 34 into inhalation gas passageway 40.

A typical capsule humidifier embodying the present invention has a rigid, cylindrical shell having an outside diameter of about 1.4 inches (3.6 cm). The hollow chamber defined by the rigid cylindrical shell preferably has a volume of about 4.6 cubic inches (75 cm$^3$). The cylindrical liquid water reservoir has an outside diameter of about 1 inch (2.54 cm) and a length of about 2.25 inches (5.4 cm). The volume of the liquid water reservoir is about 1.8 cubic inches (27 cm$^3$). During normal operation, about 30 percent to about 80 percent of the total volume is occupied by liquid water, preferably about 50 percent of total reservoir volume. The heater is a cartridge heater having a diameter of about 0.25 inch (0.63 cm) and a length of about 2 inches (5.08 cm).

In operation, breathing gas from ventilator 12 passes at a predetermined flow rate through passageway 38 and into evaporator module 18 where it entrains water vapor from liquid water reservoir 26 before entering patient inhalation passageway 40. For steady state operation, the humidifier capsule usually is maintained at about 35 degrees C. and at a liquid water flow rate of about 0.5 milliliters per minute utilizing a heater output of about 50 watts. About 30 grams of liquid water are evaporated per hour of operation. The power level for heater 28 and the rate of liquid water supplied to evaporator module 18 can also be set by breathing gas temperature controller 22.

When the temperature of the breathing gas drops, as measured by sensor 50, breathing gas temperature controller 22 responds by increasing both the power for evaporator module 18 and the flow rate setpoint for time-proportioning controller 48. In a cascade fashion, time-proportioning controller 48 increases the amount of time metering pump 46 is turned on in a given period.

Present humidifiers are preferably designed to comply with the operating requirements for inhalation therapy applications. These requirements include operating targets for breathing gas in the ranges of 30 degrees C. to 37 degrees C. and 65 to 95 percent relative humidity. The breathing gas flow rates can vary according to patient's needs and usually are in the range of about 1 liter per minute for infants up to about 30 liters per minute for adults.

With these factors accounted for, the components of the humidifier are selected or configured for related operating limits. For example, metering pump 46 preferably has a maximum flow capacity of about 50 milliliters per hour. If a higher capacity pump is used, a flow rate limit is preferably set using the pump circuitry or the time-proportioning controller. To reduce the risk of overheating, heater 28 preferably has a maximum power output of about 80 Watts. To reduce the risk of overheating, the constraint limit maintained by breathing gas temperature controller 22 for the temperature of heater 28 (measured by thermistor 54) is preferably set at about 110 to 120 degrees C.

Humidifiers embodying the present invention provide several key advantages such as flash-resistance, rainout resistance, and a relatively small gas volume. The flash-resistance makes the humidifier suitable for placement near the patient. In a preferred embodiment, the humidifier capsule is separated from the patient by at most about 70 centimeters of breathing tube. With a close connection to the patient, the risk of rainout in the tubing between the humidifier capsule and the patient is substantially reduced. The relatively small total gas volume prevents excessive dampening of ventilator pressure waves, making breathing circuit pressure profiles easier to control.

Numerous variations and modifications of the embodiments described above may be implemented without departing from the spirit and scope of the novel features of the invention. It is to be understood that no limitations with respect to the specific system illustrated herein are intended or should be inferred. It is, of course, intended to cover by the appended claims all such modifications as fall within the scope of the claims.

The invention claimed is:

1. A breathing gas humidifier capsule which comprises
an evaporator module which includes an elongated rigid shell defining a hollow chamber having a breathing gas inlet and a breathing gas outlet, a hydrophobic, water vapor permeable liquid water reservoir in the hollow chamber, said reservoir having a liquid water inlet and a liquid water outlet, and a heater situated within the liquid water reservoir and
wherein the hydrophobic, water vapor permeable liquid water reservoir is a rigid, cylindrical cage defining a plurality of rectangular windows and having a hydrophobic, water vapor permeable membrane mounted in said rectangular windows.

2. The breathing gas humidifier capsule in accordance with claim 1 wherein the liquid water reservoir is a hydrophobic mesh enclosure.

3. The breathing gas humidifier capsule in accordance with claim 2 wherein the hydrophobic mesh has a moisture vapor transmission rate of at least 15,500 grams/m2·hr.

4. The breathing gas humidifier capsule in accordance with claim 2 wherein the hydrophobic mesh has a moisture vapor transmission rate of about 20,000 to about 60,000 grams/m2·hr.

5. The breathing gas humidifier capsule in accordance with claim 1 wherein the heater is an electric resistance heater.

6. The breathing gas humidifier capsule in accordance with claim 1 wherein said liquid water inlet and said liquid water outlet are spaced from one another to maintain a liquid water free head space within the liquid water reservoir.

7. The breathing gas humidifier capsule in accordance with claim 1 wherein liquid volume in said reservoir constitutes about 30 percent to about 80 percent of total volume of the liquid water reservoir.

8. The breathing gas humidifier capsule in accordance with claim 1 wherein the elongated, hollow chamber is a cylindrical shell having a breathing gas inlet at one end and a breathing gas outlet at opposite end and wherein the liquid water reservoir is a cylindrical tube of hydrophobic mesh coaxial with the cylindrical shell and defines an annular space therebetween.

9. The breathing gas humidifier capsule in accordance with claim 1 having a breathing gas sensor at the breathing gas outlet.

10. The breathing gas humidifier capsule in accordance with claim 9 wherein the breathing gas sensor comprises dual thermistors providing a matched output.

11. A humidifier for a breathing gas comprising
an evaporator module which includes an elongated rigid shell defining a hollow chamber having a breathing gas inlet and a breathing gas outlet, a hydrophobic, water vapor permeable liquid water reservoir in the hollow chamber, said reservoir having a liquid water inlet and a liquid water outlet, and a heater situated within the liquid water reservoir;
a temperature sensor in the breathing gas outlet;
a liquid water flow controller in fluid flow communication with the liquid water inlet; and a breathing gas temperature controller operably connected to said liquid water flow controller, said heater and said temperature sensor.

12. The humidifier in accordance with claim 11 wherein said flow controller is a fixed displacement metering pump operably associated with a time-proportioning pump controller.

13. The humidifier in accordance with claim 12 wherein the metering pump is a peristaltic pump.

14. The humidifier in accordance with claim 11 wherein the temperature sensor comprises dual thermistors providing matched outputs.

* * * * *